United States Patent
Hung

(10) Patent No.: US 6,699,196 B2
(45) Date of Patent: Mar. 2, 2004

(54) SIMULATIVE ELECTRONIC BLOOD PRESSURE METER

(76) Inventor: George Hung, 1F, No. 151, Sec. 3 Pei-Shen Rd., Shen-Keng Hsiang, Taipei County (TW)

( * ) Notice: Subject to any disclaimer, the term of this patent is extended or adjusted under 35 U.S.C. 154(b) by 131 days.

(21) Appl. No.: 09/867,406

(22) Filed: May 31, 2001

(65) Prior Publication Data

US 2002/0183630 A1 Dec. 5, 2002

(51) Int. Cl.$^7$ .................................. A61B 5/0225
(52) U.S. Cl. ........................................... 600/494
(58) Field of Search ............................... 600/493–496

(56) References Cited

U.S. PATENT DOCUMENTS 4,326,536 A * 4/1982 Kitagawa et al. ............ 600/495
4,475,557 A * 10/1984 Hatschek et al. ............ 600/494
5,201,320 A * 4/1993 Barker ......................... 600/493
6,099,476 A * 8/2000 Engel .......................... 600/494

* cited by examiner

Primary Examiner—Andrew M. Dolinar
(74) Attorney, Agent, or Firm—Troxell Law Office PLLC

(57) ABSTRACT

Simulative electronic blood pressure meter in which by means of internal program, a central processor/controller converts and outputs the sensed blood pressure signal to a liquid crystal display to show a column-type indication simulating the mercury column of a traditional blood pressure meter. A digital counting circuit is combined, whereby when simulating the mercury column, an auxiliary display of digital change is provided for the user to easily know the value. The central processor/controller cooperates with a sound emitting unit which synchronously emits a sound simulating the sensed pulse from the start to the end. The volume of the emitted sound is varied with the strength of the pulse. The electronic blood pressure meter is used in a state like the mercury column-type blood pressure meter for a user to more accurately and lively judge the measured value.

4 Claims, 4 Drawing Sheets

SIMULATIVE ELECTRONIC BLOOD PRESSURE METER

BACKGROUND OF THE INVENTION

The present invention is related to a simulative electronic blood pressure meter which displays a column-type indication on a liquid crystal display to simulate the going up and down of the mercury column of a traditional blood pressure meter. A sound emitting unit is combined to synchronously emit a sound simulating the sensed pulse for a user to more accurately and lively judge the measured value.

Various kinds of electronic blood pressure meters have been developed. However, the conventional mercury column-type blood pressure meters are still widely used by doctors and nurses. This is because that the data measured by the electronic blood pressure meters often have errors due to various kinds of factors. Moreover, the electronic blood pressure meters can only show the measured value at the end of the measurement and fail to lively and accurately continuously indicate the value of the measured blood pressure during the entire measurement. Therefore, a user can hardly truly judge the measured value.

SUMMARY OF THE INVENTION

It is therefore a primary object of the present invention to provide a simulative electronic blood pressure meter which is able to display a column-type indication simulating the mercury column of a traditional blood pressure meter. A digital counting circuit is combined, whereby when simulating the mercury column, the digital change is also shown. The central processor/controller cooperates with a sound emitting unit which synchronously emits a sound simulating the sensed pulse. The volume of the emitted sound is varied with the strength of the pulse. The electronic blood pressure meter is used in a state like the mercury column-type blood pressure meter for a user to more accurately and lively judge the value of the blood pressure.

The present invention can be best understood through the following description and accompanying drawings wherein:

DETAILED DESCRIPTION OF THE PREFERRED EMBODIMENTS

Figure 1:
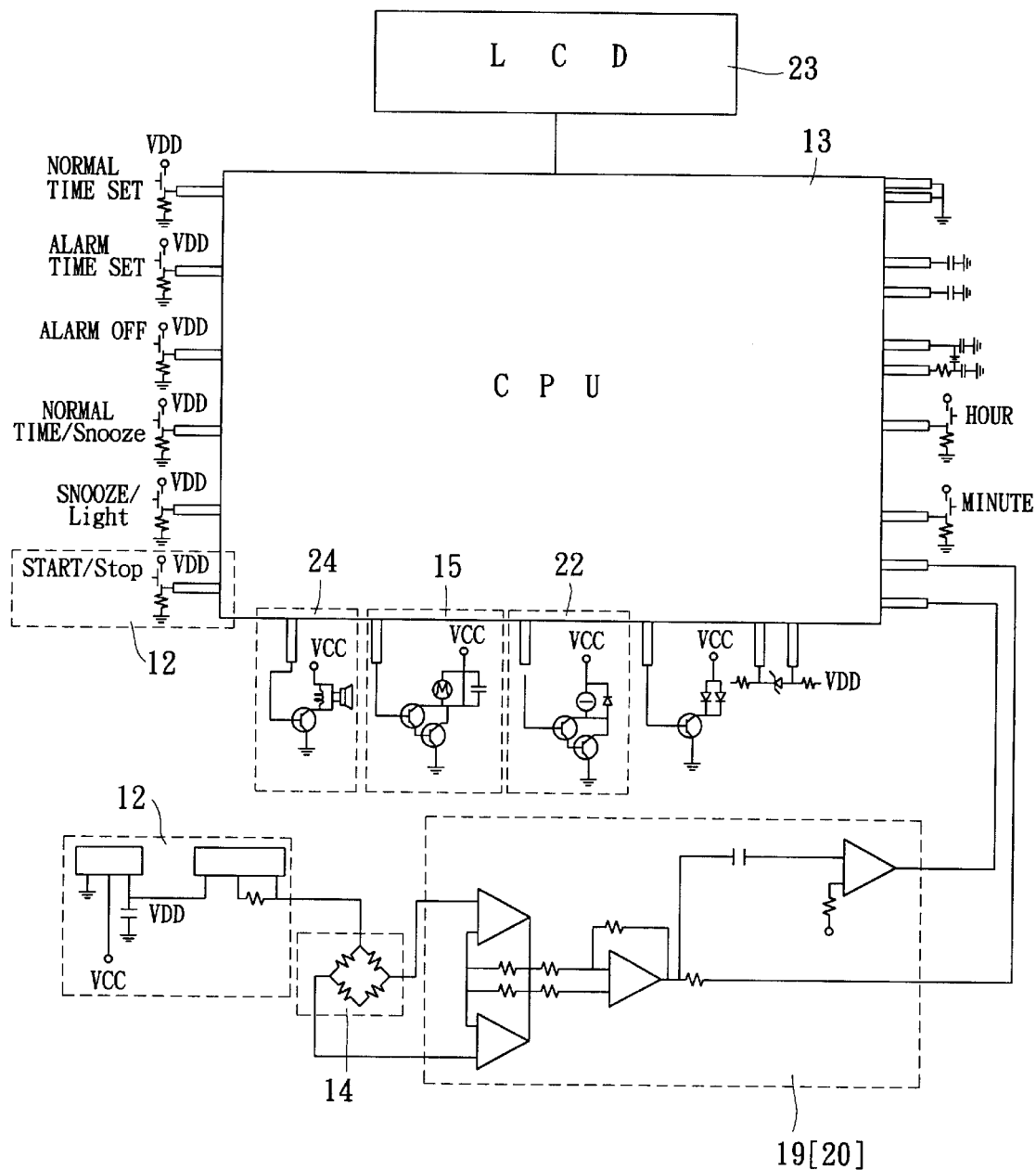
FIG. 1 is a circuit diagram of the present invention.
Figure 2:
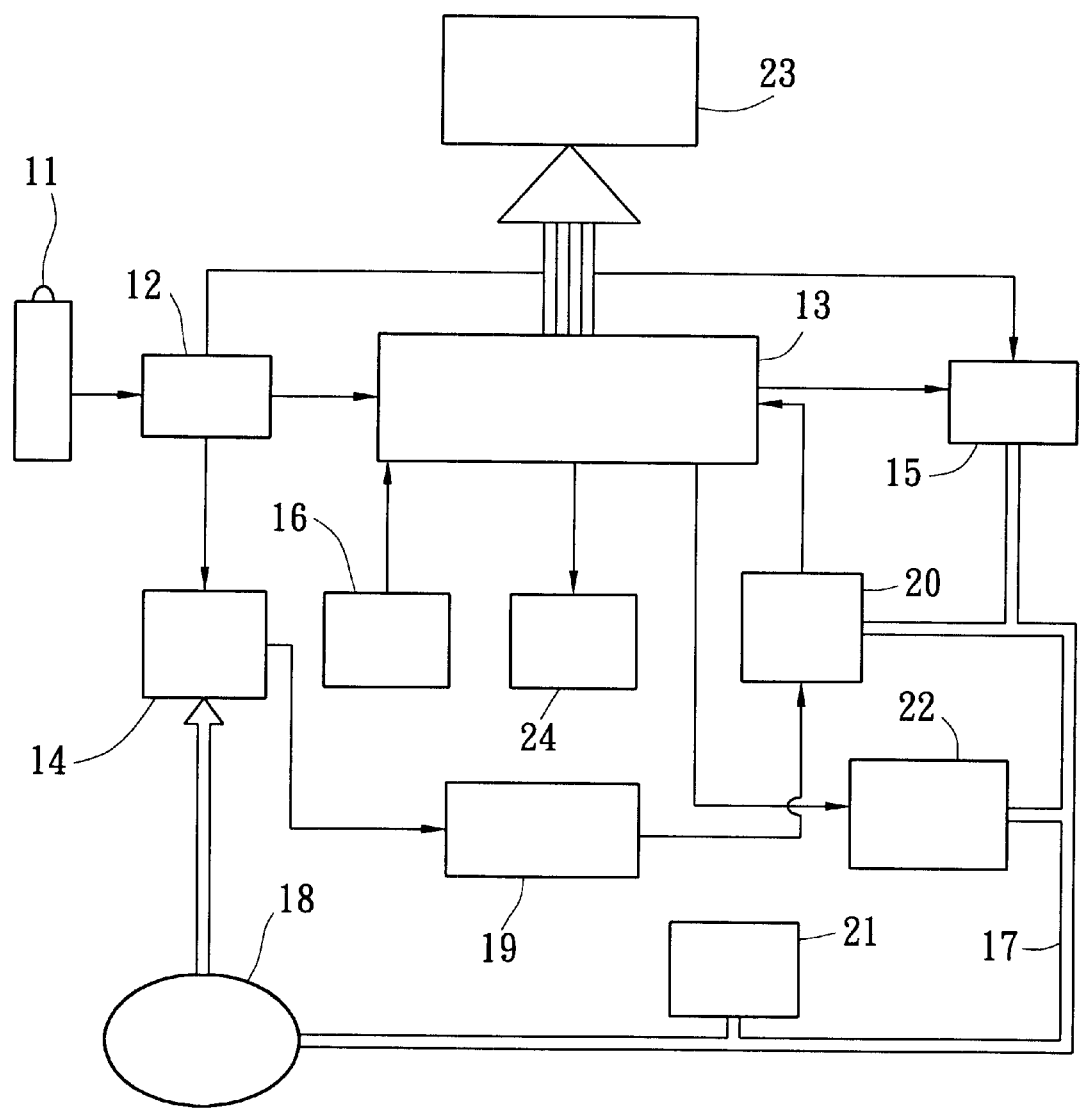
FIG. 2 is a flow chart of the circuit of the present invention.
Figure 3:
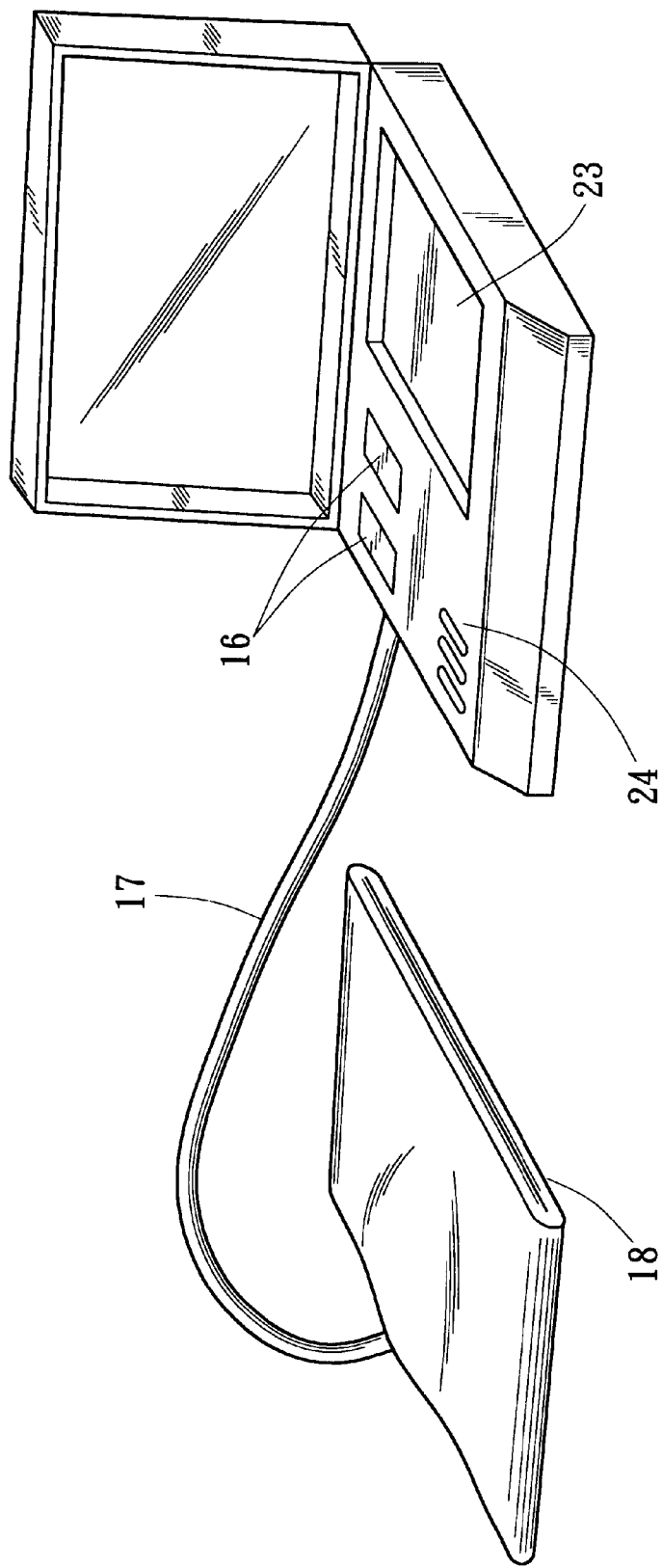
FIG. 3 is a perspective view of an embodiment of the present invention.
Figure 4:
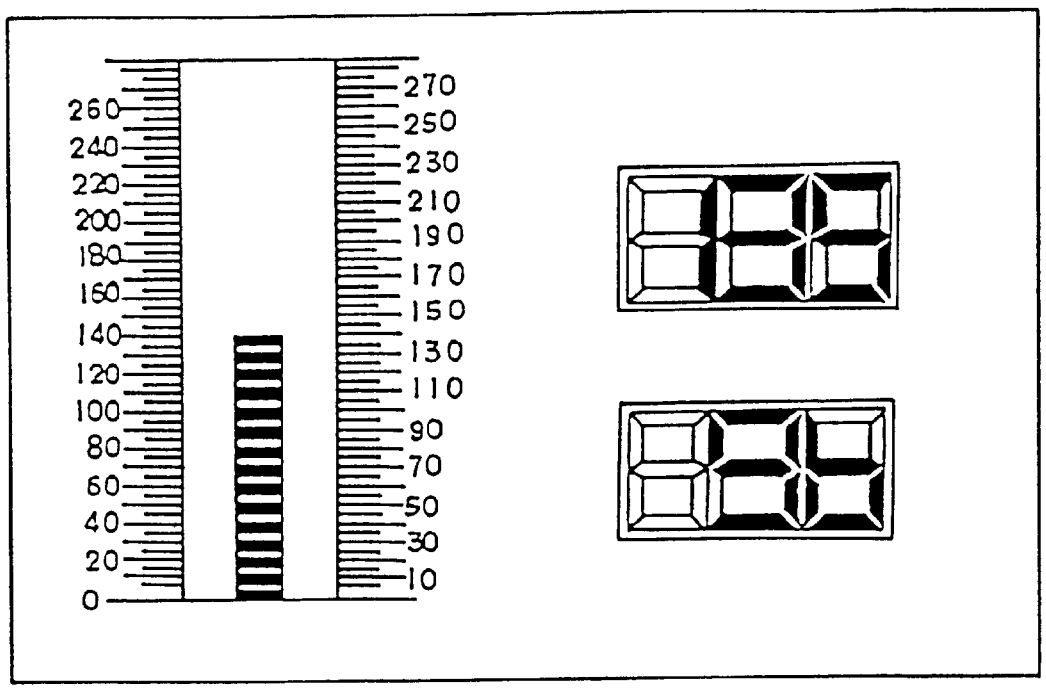
FIG. 4 is a view of the liquid crystal display of an embodiment of the present invention.

Please refer to FIG. 1. The simulative electronic blood pressure meter of the present invention includes a central processor/controller 13, a stabilizing circuit 12, a pressure sensor 14, an amplifier 19, a rectifying circuit 20, a switch keyboard 16, an electric valve 22, a display 23 and a sound emitting unit 24 which are interconnected. The central processor/controller 13 serves to open/close or analyze/process the respective units connected therewith. The stabilizing circuit 12 is connected with a cell 11 for stabilizing the power released from the cell and supplying the power to the respective circuits. The pressure sensor 14 is mounted on an inflatable envelope 18 (with reference to FIGS. 2 and 3) for sensing the pressure change of the measured object and inputting the pressure change into the amplifier 19. The amplifier 19 cooperates with the rectifying circuit 20 for amplifying and converting the pressure change into digital signal and transmitting the digital signal to the central processor/controller 13 for analysis and operation. A user operates the switch keyboard 16 to turn on/off the central processor/controller 13 or select operation options. The electric valve 22 is controlled by the central processor/controller 13 to deflate the inflatable envelope 18. The display 23 converts and displays the signal transmitted by the central processor/controller 13. The sound emitting unit 24 is controlled by the central processor/controller 13 to emit specific sound. Referring to FIG. 2, the cell 11 supplies power for the entire structure and circuit of the present invention. The stabilizing circuit 12 modulates the input voltage into a stable voltage source and respectively transmits the power to the central processor/controller 13, the pressure sensor 14 and an intake pump 15. According to the function signal indication of the switch keyboard 16, the central processor/controller 13 transmits turning on/off signal to the intake pump 15 to inflate or not to inflate the inflatable envelope 18. The intake pump 15 via an air pressure hose 17 conducts the air into a pressurizing unit surrounding the pulse measuring section such as an inflatable envelope 18. The inflatable envelope 18 is inflated until it has a fully binding pressure. At this time, the pressure sensor 14 senses the pressurized state of the inflatable envelope 18 and also senses the pulse and reactive pressure of the vessel of the bound part of the user and thus takes and transmits the pressure signal to the amplifier 19. The pressure signal is converted into current wave pattern which is rectified by the rectifying circuit 20 and transmitted to the central processor/controller 13 for analysis and processing. In the case that the expansion pressure of the inflatable envelope 18 suppresses the vessel from producing any pulse and the pressure sensor 14 cannot sense the pulse of the vessel of the bound part, the central processor/controller 13 will send out a controlling signal to the intake pump 15 to stop taking in the air. Thereafter, a constant speed exhaust valve 21 continuously exhausts the air at a constant speed of little amount, whereby the air pressure in the inflatable envelope 18 is gradually relieved. When the pressure is weakened to such a value that the pressure sensor 14 can sense that the blood in the vessel starts pulses, the pressure is gradually reduced and the pulse pressure of the blood produces pushing and squeezing action. At this time, the pressure sensor 14 can continuously sense the change of the blood pressure value change until it is unable to further sense any pulse. That is, the inflatable envelope 18 is relieved to such an extent that it cannot sense the pulse of the measured part. At this time, the measurement is completed and the central processor/controller 13 sends out a releasing signal to the electric valve 22 to control and perform fast deflation of the inflatable envelope 18. Furthermore, the blood pressure detected by the central processor/controller 13 is continuously transmitted to a liquid crystal display 23 for displaying. Referring to FIG. 4, by means of the internal program of the central processor/controller 13, the signal is converted and output to the display 23 to show a column-type indication simulating the mercury column of the mercury column of the traditional blood pressure meter. In addition, a digital counting circuit is combined, whereby when simulating the mercury column, an auxiliary display of data change is provided for the user to easily know the value. Also, the central processor/controller 13 controls a preset sound emitting unit 24. The sound emitting unit 24 synchronously emits a sound simulating the sensed pulse from the start to the end, the volume of the emitted sound is varied with the strength of the pulse. With the sound, the user can more accurately and easily judge the measured value.

The above embodiments are only used to illustrate the present invention, not intended to limit the scope thereof. Many modifications of the above embodiments can be made without departing from the spirit of the present invention.

What is claimed is:

1. A simulative electronic blood pressure meter comprising:
   a) a central processor controlling an intake pump;
   b) a pressurizing unit having an inflatable envelop and a tube system;
   c) the intake pump pressurizing the pressurizing unit such that the pressurizing unit pressurizes a vessel;
   d) a pressure sensor sensing a blood pressure in the vessel pressurized by the pressurizing unit, the pressure sensor outputting a corresponding blood pressure signal to the central processor for conversion and processing;
   e) a switch keyboard controlling the central processor;
   f) a display having a liquid crystal display, a simulated mercury column of a traditional blood pressure meter, and a digital counting circuit, the display receiving a display signal from the central processor for display, such that the display includes the simulated mercury column and an auxiliary display of digital change; and
   g) a sound emitting device receiving a sound signal from the central processor and emitting an audible sound representing a pulse sensed by the pressure sensor from the vessel under pressure by the pressurizing unit, a volume of the sound is varied to correspond with a strength of the pulse.

2. The simulative electronic blood pressure meter according to claim 1, further comprising:
   a) a cell providing power; and
   b) a stabilizing unit modulating the power provided by the cell to provide a stable voltage source to the simulative electronic blood pressure meter.

3. The simulative electronic blood pressure meter according to claim 1, further comprising:
   a) an amplifier receiving a pulse signal from the pressure sensor, the amplifier processing and converting the pulse signal into an electric wave pattern; and
   b) a rectifier receiving the electric wave pattern from the amplifier, wherein the electric wave pattern is rectified by the rectifier and transmitted to the central processor for processing and controlling.

4. The simulative electronic blood pressure meter according to claim 1, further comprising an electric valve connected to the pressurizing unit and controlled by the central processor, wherein, when the pressure sensor is unable to sense the pulse from the vessel under pressure by the pressurizing unit, the central processor opens the electric valve.

* * * * *